(12) United States Patent
Saaski

(10) Patent No.: US 8,881,574 B2
(45) Date of Patent: Nov. 11, 2014

(54) SHIPPING CONTAINER INTERROGATION APPARATUS AND METHODS

(75) Inventor: Elric W. Saaski, Bothell, WA (US)

(73) Assignee: Research International, Inc, Monroe, WA (US)

(*) Notice: Subject to any disclaimer, the term of this patent is extended or adjusted under 35 U.S.C. 154(b) by 1510 days.

(21) Appl. No.: 12/460,782

(22) Filed: Jul. 24, 2009

(65) Prior Publication Data

US 2010/0186483 A1 Jul. 29, 2010

Related U.S. Application Data

(63) Continuation-in-part of application No. 12/231,207, filed on Aug. 29, 2008.

(51) Int. Cl.
- *G01N 7/00* (2006.01)
- *G01N 1/22* (2006.01)
- *G01N 1/00* (2006.01)
- *G01N 1/02* (2006.01)

(52) U.S. Cl.
CPC ........ *G01N 1/2226* (2013.01); *G01N 2001/022* (2013.01); *G01N 2001/2223* (2013.01)
USPC .............................. 73/31.03; 73/863; 73/23.2

(58) Field of Classification Search
CPC ................ G01N 2001/022; G01N 2001/2223; G01N 1/24; G01N 1/2226; G01N 2001/025
USPC .......... 73/23.2, 40.7, 863.83, 864.73, 863.81, 73/31.01, 31.02, 863, 31.03; 220/560.07; 206/335
See application file for complete search history.

(56) References Cited

U.S. PATENT DOCUMENTS

| | | | | |
|---|---|---|---|---|
| 2,702,458 A | * | 2/1955 | Del Mar | 62/59 |
| 2,968,933 A | * | 1/1961 | Pfeifer et al. | 62/176.6 |
| 3,619,616 A | * | 11/1971 | Smith | 250/506.1 |
| 4,580,440 A | | 4/1986 | Reid et al. | |
| 4,718,268 A | | 1/1988 | Reid et al. | |
| 5,347,845 A | | 9/1994 | Kepler | |
| 6,446,514 B1 | | 9/2002 | Danylewych-May et al. | |
| 6,792,795 B2 | | 9/2004 | Jones et al. | |

(Continued)

FOREIGN PATENT DOCUMENTS

| | | |
|---|---|---|
| CN | 101316773 A | 12/2008 |
| WO | WO 03/081214 A2 | 10/2003 |

OTHER PUBLICATIONS

U.S. Appl. No. 12/231,207, filed Aug. 29, 2008 for a Concentrator invented by Elric W. Saaski and Charles C. Jung.

(Continued)

*Primary Examiner* — Peter Macchiarolo
*Assistant Examiner* — Jamar Ray
(74) *Attorney, Agent, or Firm* — Gregory W. Moravan

(57) ABSTRACT

A shipping container interrogation apparatus and method that utilizes the tubular frame members of the container to deliver input air to the interior of the container, and to receive sample air from the interior of the container. A detection apparatus may be used to detect an unauthorized material in the sample air that is received from the interior of the container. Sample air from the detection apparatus may be recycled back into the container by use of a tubular frame member of the container. Input air may be delivered to the interior of the container with turbulence and in any desired direction or pattern for better interrogation of the interior of the container.

29 Claims, 10 Drawing Sheets

(56) References Cited

U.S. PATENT DOCUMENTS

| | | |
|---|---|---|
| 6,823,714 B2 | 11/2004 | Megerle |
| 6,978,657 B1 | 12/2005 | Baumann et al. |
| 7,019,640 B2 | 3/2006 | Canich et al. |
| 7,032,467 B2 | 4/2006 | Yoon |
| 7,100,424 B2 | 9/2006 | Wilson |
| 7,151,447 B1 | 12/2006 | Willms et al. |
| 7,158,028 B1 | 1/2007 | Ghahramani |
| 7,188,513 B2 | 3/2007 | Wilson |
| 7,216,548 B2 | 5/2007 | Kurita et al. |
| 7,316,152 B2 | 1/2008 | Strohmeyer et al. |
| 7,324,921 B2 | 1/2008 | Sugahara et al. |
| 7,394,363 B1 | 7/2008 | Ghahramani |
| 7,468,672 B2 | 12/2008 | Harden et al. |
| 7,501,624 B1 | 3/2009 | Farrell et al. |
| 7,503,204 B2 | 3/2009 | Strohmeyer et al. |
| 2004/0020267 A1 | 2/2004 | Megerle |
| 2004/0045342 A1 | 3/2004 | Jones et al. |
| 2004/0226342 A1 | 11/2004 | Taricco |
| 2004/0233055 A1 | 11/2004 | Canich et al. |
| 2005/0081653 A1 | 4/2005 | Arabian et al. |
| 2006/0027751 A1 | 2/2006 | Kurita et al. |
| 2006/0042397 A1 | 3/2006 | Kurita et al. |
| 2006/0169025 A1 | 8/2006 | Wilson |
| 2006/0226998 A1 | 10/2006 | Wilson |
| 2006/0257287 A1 | 11/2006 | Call et al. |
| 2007/0266771 A1 | 11/2007 | Goldson et al. |
| 2007/0277589 A1 | 12/2007 | Harden et al. |
| 2008/0055075 A1 | 3/2008 | Fano |
| 2008/0129493 A1 | 6/2008 | Fuentes et al. |
| 2008/0251514 A1 | 10/2008 | Fitzpatrick |
| 2009/0184818 A1 | 7/2009 | Murphy et al. |
| 2010/0050750 A1 | 3/2010 | Saaski et al. |

OTHER PUBLICATIONS

English translation of reference AU, First Office Action, including search report, for corresponding Chinese patent application No. 201210299533.5, issued Jan. 20, 2014, 8 pages.

First Office Action, including search report, for corresponding Chinese patent application No. 201210299533.5, issued Jan. 20, 2014, 6 pages.

* cited by examiner

SHIPPING CONTAINER INTERROGATION APPARATUS AND METHODS

This is a continuation-in-part of U.S. application Ser. No. 12/231,207 filed on Aug. 29, 2008. Under 37 CFR 1.57 the forgoing parent Application is hereby incorporated by reference into this Application.

DETAILED DESCRIPTION OF THE INVENTION

Shipping Containers 10

Referring now to the Figures, a serious worldwide problem at seaports, airports, and other shipping facilities is that shipping containers 10 may contain unauthorized materials such as contraband, drugs, explosives, biowarfare materials, or radioactive materials.

Accordingly, apparatus and methods are needed that will efficiently interrogate sample air from the containers 10 for any unauthorized materials. By interrogation, it is meant that sample air from within the containers 10 may be received from the containers 10 so that any gasses or any airborne particles from the unauthorized materials that are in the sample air may be made available for collection, observation, identification, examination, testing or analysis by any suitable detection apparatus 53.

It is to be understood that when the detection apparatus 53 is said to be operable to detect any unauthorized material in the sample air, it is meant that the detection apparatus is operable to collect any such unauthorized material, and is operable to be used to observe, identify, examine, test or analyze any such unauthorized material.

Such airborne particles from the unauthorized materials may be termed "airborne particles containing target material", and may be any liquid, solid, organic, inorganic, biological or non-biological material, or mixtures thereof. The airborne particles containing target material may, or may not, comprise materials other than target material.

The term "air" is used broadly, so that it may be any gas or mixture of gasses other than air.

By way of non-limiting example, in the discussion which follows the apparatus and methods of the present invention will be disclosed as being used with a typical ocean-going shipping container 10. However, it is understood that the apparatus and methods of the present invention may be used with any kind of shipping container 10, ocean-going or not, large or small, that has a frame 18 that at least partially comprises tubular frame members 19-23.

The tubular frame members 19-23 may have any geometric or non-geometric cross-sectional configuration such as square, rectangular or circular.

Figure 1:
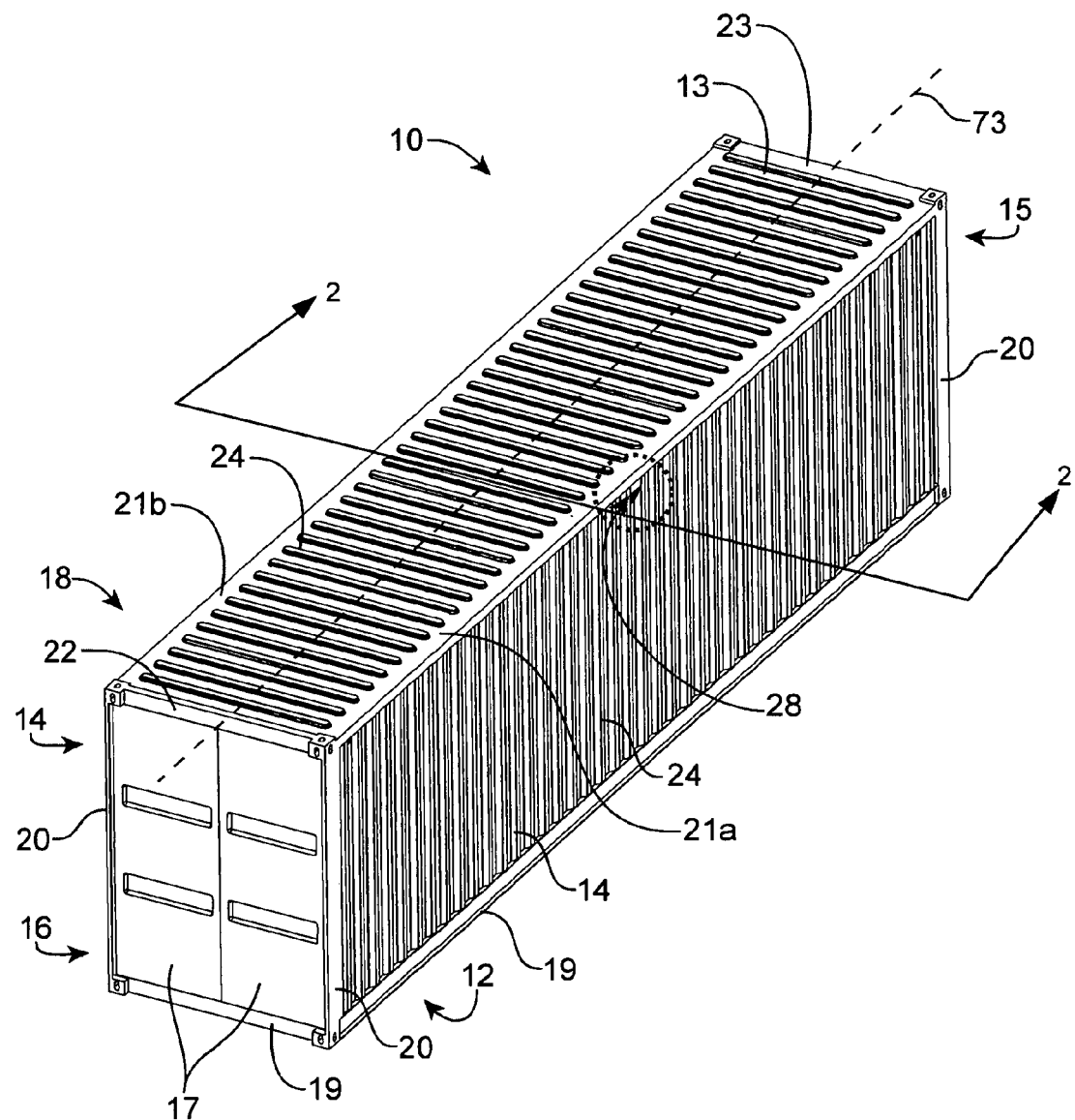
FIG. 1 is a perspective view of the exterior of a shipping container 10 showing an exterior port 28 installed therein.

As seen in FIG. 1, the container 10 may comprise a bottom 12; a top wall 13; a pair of sidewalls 14; a back wall 15; a front wall 16, which may be equipped with one or more doors 17; and a frame 18.

Structural rigidity and shape for the container 10 may be at least partially provided by its frame 18. Its frame 18 may be of any suitable size, shape, and construction, and may comprise, for example, peripheral left, right, front and back bottom frame members 19; a corner frame member 20 at each of the four corners of the container 10; left and right top, side frame members 21a, 21b, a front top frame member 22, and a back top frame member 23. The frame members 19-23 may be connected together in any suitable way such as by welding or by the use of fasteners. The top, side frame members 21a, 21b may comprise part of their respective sidewalls 14 of the container 10.

Any or all of the frame members 19-23 may be made from tubular material, such as the tubular frame members 21a, 21b. Even though the bottom frame members 19 are illustrated as comprising I-beams, even the bottom frame members 19 may be made from tubular material.

The walls 13-15 of the container 10 may typically comprise corrugated material 24 that may be secured to the frame 18 in any suitable way, such as by welding or by the use of fasteners.

A container 10 may typically comprise an unused top airspace 25 that lies between the top of the cargo 26 and the inside of the container 10's top wall 13. The top airspace 25 may vary in size, depending on how high the cargo 26 is stacked within the container 10. However, even when the container 10 is nominally full of cargo 26, a top air space 25 will normally exist, since it may be relatively rare for the cargo 26 in the container 10 to fill the container 10 completely to its top wall 13.

A container 10 may also typically comprise one or more lateral airspaces 27 that are located between the cargo 26 and one or more of the container 10's sidewalls 14, back wall 15, or front wall 16. In addition, if one or more of the walls 14-16 comprise corrugated material 24, then even if the cargo 26 extends to one or more of the walls 14-16, lateral airspaces 27 may be provided between the cargo 26 and the adjacent wall 14-16 by the concave portions of the corrugated material 24.

It will be appreciated that if there were a way to receive sample air from the container 10's top or lateral air spaces 25, 27, then any gasses or any airborne particles that are in the sample air from any unauthorized materials in the container 10 may be made available for collection, observation, identification, examination, testing or analysis by any suitable detection apparatus 53.

It has been discovered that if any of the frame members 19-23 are tubular, then one or more of such tubular frame members 19-23 may be used as an air transfer tubular frame member 19-23 or air duct 19-23 to: (a) receive sample air from within the container 10's top or lateral air spaces 25, 27 for collection, observation, identification, examination, testing or analysis by any suitable detection apparatus 53; (b) to convey fresh air into the interior 66 of the container 10; or (c) to convey into the interior 66 of the container 10 sample air that was previously received from the container 10 (i.e., to recycle such sample air back into the container 10), in order to help prevent contamination of the environment around the container 10 by any hazardous materials from any unauthorized materials within the interior 66 of the container 10 that may be carried by the sample air.

By way of non-limiting example, in the discussion that follows it will be assumed that the frame members 21a, 21b are tubular frame members 21a, 21b that may act as air ducts. However, it is to be understood that all of the same, or similar comments, made herein regarding the tubular frame members 21a, 21b; regarding their exterior and interior ports 28, 47; and regarding the use of members 21a, 21b and ports 28, 47 as part of a container interrogation apparatus may apply equally well regarding any of the other frame members 19-20 and 22-23 that may be tubular and that may act as air ducts.

Each tubular frame member 21a, 21b may have a top side 29, a bottom side 30, an exterior side 31, and an interior side 32; and may define an air cavity 41.

The interior dimensions of the tubular frame members 21a, 21b of a typical ocean-going shipping container 10 may be on the order of 5 to 7 cm in height and/or width. As a result, such a tubular frame member 21a, 21b may act as an air duct that may be able to transport thousands of liters per minute of air axially along its length for many meters with only modest pressure drops.

For example, if a tubular frame member 21a, 21b had a square internal cross-sectional configuration with an area of about 49 cm$^2$ then it may be readily calculated that such a tubular frame member 21a, 21b would be able to transport an airflow of about 2,000 liters/minute over a length of 6 meters with only about a 0.5 mmHg pressure difference over that length. Air pressure differences of this magnitude may be readily produced with conventional centrifugal blowers of the type used in heating and ventilation applications.

Since a typical ocean-going container 10 may have a volume on the order of about 50,000 liters, it is apparent that interrogation of a very large volume of sample air from the container 10 may by accomplished in a very short period of time by using the tubular frame members 21a, 21b as air ducts. For example, if an airflow of sample air is delivered by the tubular frame members 21a, 21b to the detection apparatus 53 at the rate of about 8,000 liters/minute, a volume of sample air from about 8,000 liters up to about 24,000 liters may be delivered to the detection apparatus in as little as about 1 to 3 minutes.

In a modern seaport, which may handle hundreds or even thousands of containers 10 per day, it is apparent that it may be important to obtain large volumes of sample air from each container 10 in as short a period of time as may be reasonably possible, in order to increase the speed, sensitivity or accuracy of interrogation of each container 10 for unauthorized materials, and in order to increase the number of containers 10 that may be interrogated in any given period of time.

Exterior Ports 28

A tubular frame member 21a, 21b may be provided with any suitable air transfer exterior port 28 of any suitable size, shape, dimensions, construction and location, for providing fluid communication between the air cavity 41 of a tubular frame member 21a, 21b and the exterior of the container 10. All of the various embodiments of the exterior port 28 that are described or illustrated herein are by way of non-limiting example.

Any particular exterior port 28 may be used to receive sample air from a tubular frame member 21a, 21b; to deliver fresh air to a tubular frame member 21a, 21b; or to deliver to a tubular frame member 21a, 21b sample air that has been previously received from the container 10.

It is understood that if a particular exterior port 28 is described or illustrated with respect to a particular tubular frame member, such as tubular frame member 21a, for example, then same comments and illustrations regarding that exterior port 28 will apply equally well with respect to a tubular frame member 21b, and vice versa.

An exterior port 28 may access the air cavity 41 of a tubular frame member 21a, 21b through any of its sides 29-32. When a particular exterior port 28 is described or illustrated as accessing an air cavity 41 through a particular one of the sides 29-32 of a tubular frame member 21a, 21b, it is understood that that particular exterior port 28 may be easily modified, if needed, to access the air cavity 41 through any of the other sides 29-32 of a tubular frame member 21a, 21b.

Although only one exterior port 28 is illustrated for each of the two tubular frame members 21a, 21b, one or more of the tubular frame members 21a, 21b may have more than one exterior port 28.

Each exterior port 28 may be located in any suitable location along the length of its respective tubular frame member 21a, 21b. If a tubular frame member 21a, 21b has only one exterior port 28, then it may be advantageous to centrally locate the exterior port 28 along the length of the tubular frame member 21a, 21b, if it is desired to minimize the pressure drops along the length of the tubular frame member 21a, 21b.

On the other hand, if a particular tubular frame member 21a, 21b has more than one exterior port 28, then the exterior ports 28 may be located at any desired regular or irregular intervals along the length of the tubular frame member 21a, 21b, and may be located at any suitable places along the length of the tubular frame member 21a, 21b. The number, interval and location of the exterior ports 28 of a particular tubular frame member 21a, 21b may be selected depending on the applicable variables, such as the respective lengths and volumes of the container 10 and the tubular frame member 21a, 21b; how rapidly it is desired to receive the sample air from the container 10; and the number and size of the air pumps 49, 51 available to be connected to the exterior ports 28.

Figure 4:
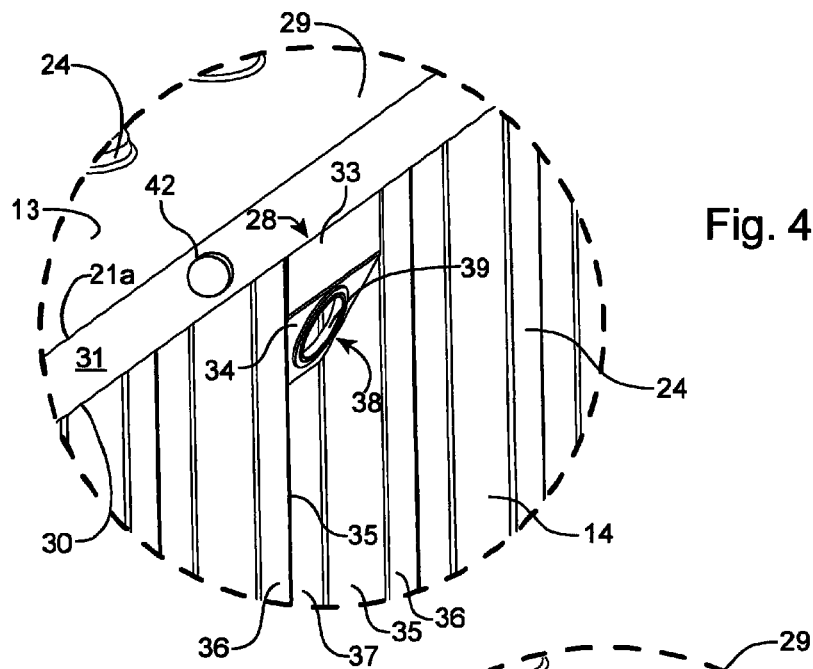
FIG. 4 is an enlarged view of the circled portion of FIG. 1.

As seen in FIG. 4, the simplest kind of exterior port 28 may comprise a port hole 42 in any of the sides 29-32 of the tubular frame member 21a, such as in its exterior side 31, for example. The port hole 42 may comprise any suitable optional gasket for providing a seal with whatever object may be connected to it, and may further comprise any suitable optional removable or non-removable cover for preventing the entry of rain or foreign matter into it.

Figure 2:
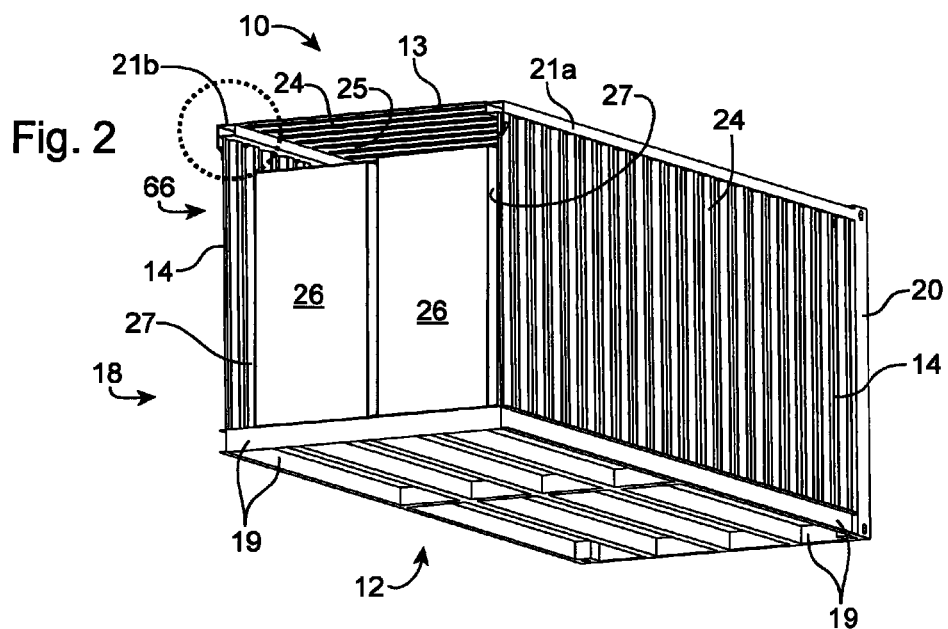
FIG. 2 is a perspective cross-sectional view of the container 10 taken along line 2-2 of FIG. 1.
Figure 3:
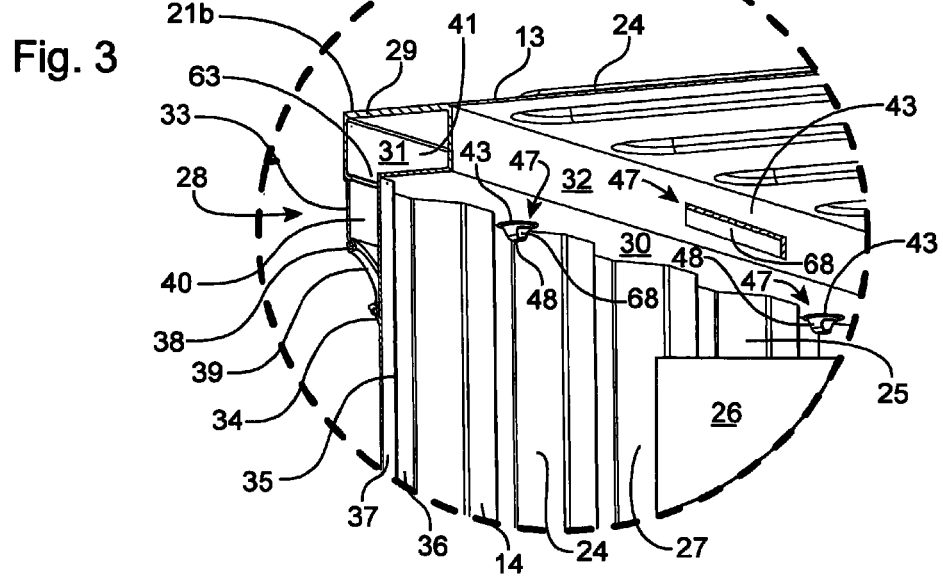
FIG. 3 is an enlarged view of the circled portion of FIG. 2.

Another embodiment of an exterior port 28 is illustrated in FIGS. 1-3 with respect to tubular frame member 21b, and in FIG. 4 with respect to tubular frame member 21a. Such an exterior port 28 may comprise, for example, a top plate 33 and a bottom plate 34 which may be secured to the container 10 in any suitable way such as by welding, adhesives or fasteners.

The top plate 33's top edge may be secured to the tubular frame member 21b's bottom side 30 or exterior side 31; and the top plate 33's lateral edges may be secured to respective adjacent corrugation sides 35 or corrugation exterior portions 36 of the corrugated material 24 of the container 10's sidewall 14.

The bottom plate 34's top edge may be secured to the top plate 33's bottom edge; the bottom plate 34's lateral edges may be secured to respective adjacent corrugation sides 35 or corrugation exterior portions 36 of the corrugated material 24; and the bottom plate 34's bottom edge may be secured to a corrugation interior portion 37 of the corrugated material 24. The bottom plate 34 may be oriented so that its top edge is further away from the corrugation interior portion 37 of the corrugated material 24 than is its bottom edge.

The top and bottom plates 33, 34 and the adjacent portions of the corrugated material 24's corrugation sides 35, corrugation exterior portions 36 and corrugation interior portion 37 may form an exterior air input/sample air output air plenum 40. As best seen in FIG. 3, the upper end of the plenum 40 may be in fluid communication with the air cavity 41 of the tubular frame member 21b through a port 63 in the bottom side 30 of the tubular frame member 21b.

The exterior port 28 may also comprise a port hole 38 that may be located in the bottom plate 34. Alternatively, the port hole 38 may be located in the top plate 33.

The port hole 38 may comprise any suitable optional gasket 39 for helping to form a seal with whatever object may be connected to it, and may further comprise any suitable optional removable or non-removable cover for preventing the entry of rain or foreign matter into it.

As best seen in FIG. 4, the inward tipping of the bottom plate 34, and its location between a pair of adjacent corrugation exterior portions 36 of the corrugated material 24, enables the top plate 33 and the pair of adjacent corrugation exterior portions 36 of the corrugated material 24 to help prevent the entry of rain or foreign matter into the port hole 38.

Figure 5:
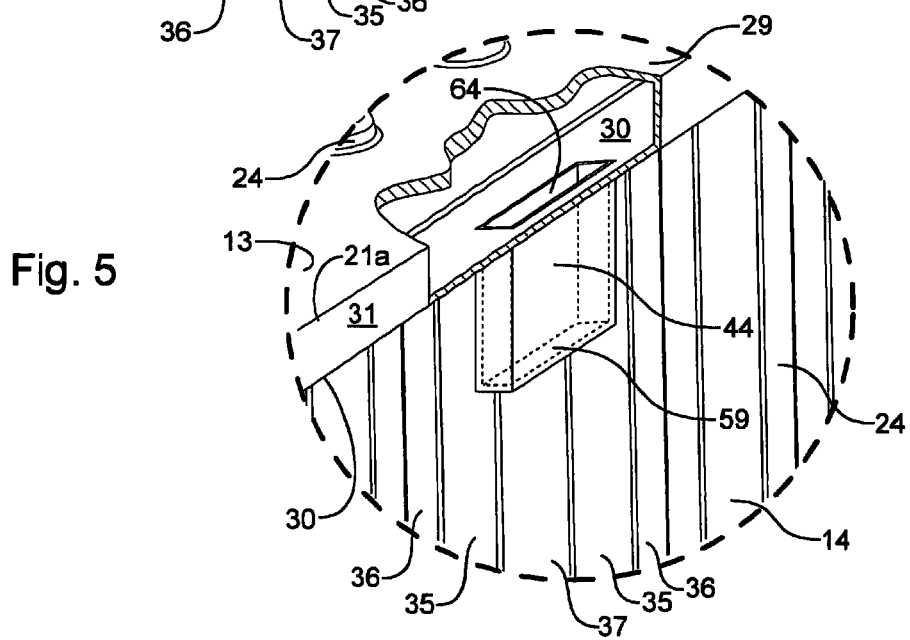
FIG. 5 is a view similar to FIG. 4, which illustrates another embodiment of an exterior port 28.

Referring now to FIG. 5, a further alternative form of the exterior port 28 is illustrated which may comprise any suitable tubular element 44 that may be secured over a port 64 in the bottom side 30 of the tubular frame member 21a, so that the tubular element 44 is in fluid communication with the air cavity 41 of the tubular frame member 21a. The tubular element 44 may have any suitable size, shape, dimensions, cross-sectional configuration, construction and location. The tubular element 44 may be located between a pair of adjacent corrugation exterior portions 36 of the corrugated material 24.

The bottom of the tubular element 44 may be open to form a port hole 59 that is in fluid communication with the air cavity 41 of the tubular frame member 21a via the tubular element 44. Alternatively, the bottom end of the tubular element 44 may be closed and a port hole 59 may be located in one of the sides of the tubular element 44. The port hole 59 may comprise any suitable optional gasket for helping to form a seal with whatever object may be connected to it, and may further comprise any suitable optional removable or non-removable cover for preventing the entry of rain or foreign matter into it.

Interior Ports 47

A tubular frame member 21a, 21b may be provided with one, or more than one, of any suitable air transfer interior port 47 of any suitable size, shape, dimensions, construction, and location, for providing fluid communication between the air cavity 41 of a tubular frame member 21a, 21b and the interior 66 of the container 10. All of the various embodiments of the interior ports 47 that are described or illustrated herein are by way of non-limiting example.

Any particular interior port 47 may be used to receive sample air from the container 10's interior 66, to deliver fresh air to the container 10's interior 66, or to deliver to the container 10's interior 66 sample air that has been previously received from the container 10.

It is understood that if a particular interior port 47 is described or illustrated with respect to a particular tubular frame member, such as tubular frame member 21a, for example, then same comments and illustrations regarding that interior port 47 will apply equally well with respect to a tubular frame member 21b, and vice versa.

An interior port 47 may access the air cavity 41 of a tubular frame member 21a, 21b through any of its sides 29-32. When a particular interior port 47 is described or illustrated as accessing an air cavity 41 through a particular one of the sides 29-32 of a tubular frame member 21a, 21b, it is understood that that particular interior port 47 may be easily modified, if needed, to access the air cavity 41 through any of the other sides 29-32 of a tubular frame member 21a, 21b.

Each interior port 47 may be located in any suitable place along the length of the tubular frame member 21a, 21b. If a tubular frame member 21a, 21b has only one interior port 47, then it may be advantageous to centrally locate the interior port 47 along the length of the tubular frame member 21a, 21b, to maximize its lateral access to the interior space 66.

On the other hand, if a tubular frame member 21a, 21b has more than one interior port 47, then the interior ports 47 may be located at any desired regular or irregular intervals along the length of the tubular frame member 21a, 21b, and may be located at any suitable place along the length of the tubular frame member 21a, 21b. The number, interval and location of the interior ports 47 may be selected depending on the applicable variables, such as the length and volume of the container 10 and the tubular frame member 21a, 21b, how rapidly it is desired to receive the sample air from the container 10, and in what directions and patterns it is desired to have the input air delivered to the container 10 sweep the interior 66 of the container 10.

As seen in FIG. 3, the simplest kind of interior port 47 may comprise a port hole 43 in any of the sides 29-32 of the tubular frame member 21b, such as in its bottom side 30, or interior side 31, for example. The port hole 43 may comprise any suitable optional gasket for helping to form a seal with whatever object may be connected to it, and may further comprise any suitable optional removable or non-removable cover for preventing the entry of foreign matter into it.

As seen in FIG. 3, an interior port 47 may further comprise an optional passive or an active nozzle 48 of any suitable size, shape and construction. If the interior port 47 is used to deliver fresh air or recycled sample air to the interior 66 of the container 10, then the nozzle 48 may be an air input nozzle 48 and may be used, for example, for directing any input air delivered from the nozzle 48 in any desired predetermined flow direction or predetermined flow pattern within the container 10, such as within its top airspace 25 or within one or more of its lateral air spaces 27. For more thorough interrogation of the container 10, the nozzle 48 may also be used, for example, to impart any desired predetermined turbulent flow characteristic to the air it delivers to the interior 66 of the container 10. Such turbulent air may be beneficial in, for example, helping any particles of any unauthorized material on the interior 66 of the container 10 or on the exterior of the cargo 26 to become entrained in the sample air that is then received from interior 66 of the container 10; and in helping any gasses from any unauthorized material in the interior 66 of the container 10 to become mixed with the sample air that is then received from the interior 66 of the container 10.

On the other hand, if the interior port 47 is used to receive sample air from the interior 66 of the container 10, then the nozzle 48 may be a sample air output nozzle 48 and may be used, for example, to receive sample air from any desired flow direction. Alternatively, such an interior port 47 may not have a nozzle 48.

For more thorough interrogation of the container 10, the nozzles 48 may be constructed and located so that the incoming air they deliver to the interior 66 of the container 10 sweeps relatively uniformly over all of the cargo 26 in the container 10 to the extent reasonably practical, depending on the relevant factors such as the nature, quantity, shape, packing density and volume of the cargo 26 in the container 10.

Each nozzle 48 may, or may not, be of the same or similar construction as one or more of the other nozzles 48; each nozzle 48 that expels air may, or may not, direct the air that it delivers in the same flow direction or flow pattern within the interior 66 of the container 10 as one or more of the other nozzles 48; and each nozzle 48 that receives sample air from the interior 66 of the container 10 may not receive the sample air from the same flow direction as one or more of the other nozzles 48.

A passive nozzle 48 is illustrated in FIGS. 2-3. However, an active nozzle 48 may be used which has any suitable controls and construction for actively moving the nozzle 48 in any desired direction or pattern, so that it may direct any air that it delivers in any desired flow direction or flow pattern within the interior 66 of the container 10, such as within its top airspace 25 or lateral air spaces 27; or so that it may receive any sample air from the interior 66 of the container 10 from any desired flow direction or directions.

Interrogation Using Two Tubular Frame Members 21A, 21B

Figure 6:
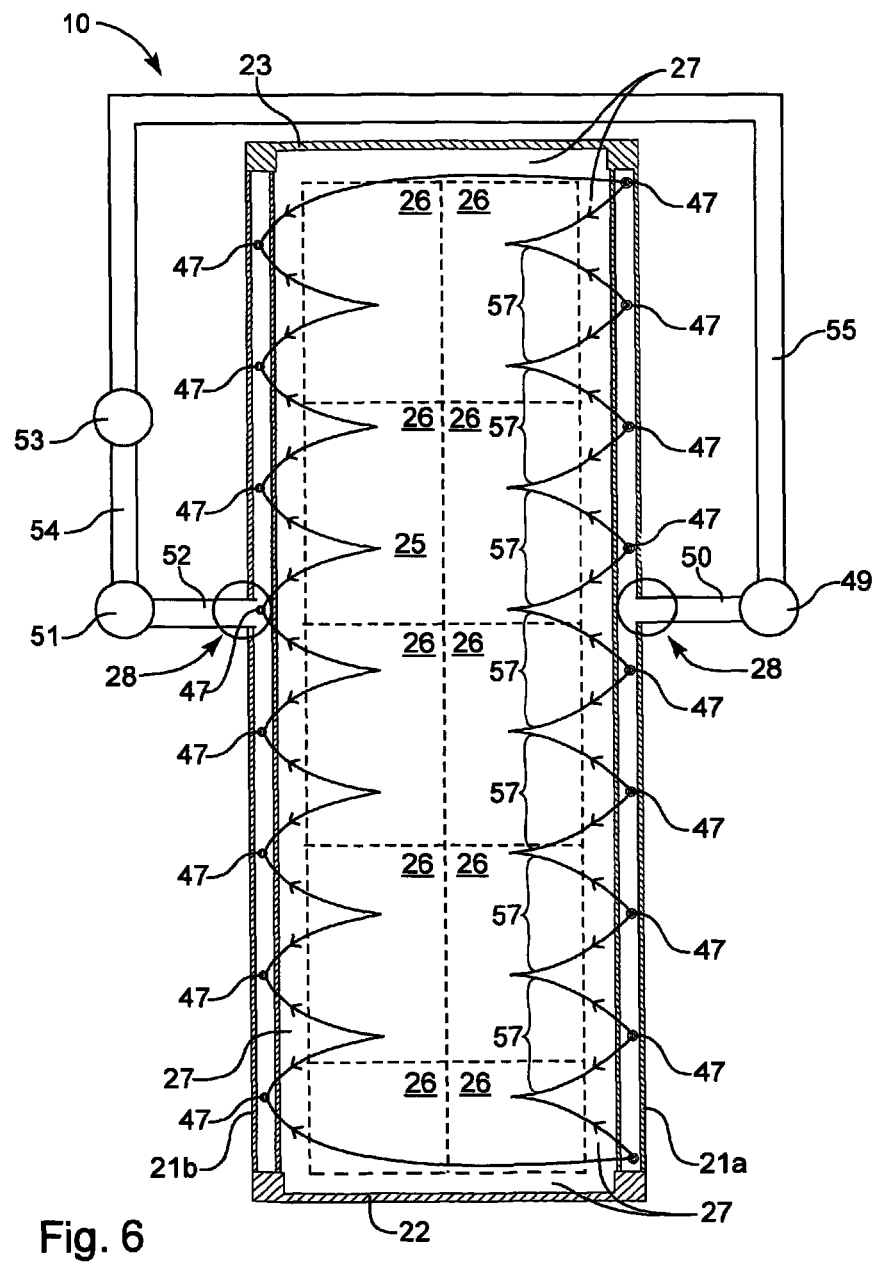
FIG. 6 is a top elevational view of the container 10 with its top wall 13 removed, showing air flows 57 within the container 10, and also showing various ancillary apparatus used during interrogation of the container 10 by two tubular frame members 21a, 21b.

Referring now to FIG. 6, interrogation of the container 10 by using two tubular frame members 21a, 21b will now be described. Each tubular frame member 21a, 21b may be used as either an air input tubular frame member 21a, 21b or as a sample air output tubular frame member 21a, 21b.

By way of example, let it be assumed that tubular frame member 21a is an air input tubular frame member 21a which may be used to deliver to the interior 66 of the container 10 either fresh air, or sample air that has been previously received from the container 10 (i.e., recycled sample air).

Let it be further assumed that tubular frame member 21b is a sample air output tubular frame member 21b that may be used to receive sample air from the interior 66 of the container 10; and that the air input and the sample air output tubular frame members 21a, 21b both have exterior and interior ports 28, 47.

Any suitable number of any suitable air pumps 49, 51 may be connected in any suitable combination in any suitable way to the exterior ports 28 of the air input and sample air output tubular frame members 21a, 21b to deliver input air into the interior 66 of the container 10, and to receive sample air from the interior 66 of the container 10.

By way of example, FIG. 6 illustrates a container 10 in which the air input tubular frame member 21a has one centrally located air input exterior port 28 and nine air input interior ports 47. The sample air output tubular frame member 21b has eight sample air output interior ports 47 and one centrally located sample air output exterior port 28.

Although only one form of exterior and interior ports 28, 47 is illustrated in FIG. 6, the exterior and interior ports 28, 47 may comprise any of the embodiments of the exterior and interior ports 28, 47 that are described herein. It may be desirable to position at least some of the sample air output interior ports 47 of the sample air output tubular frame member 21b at positions along its length that are intermediate to positions of the air input interior ports 47 along the length of the air input tubular frame member 21a, so as to create a more uniform flow of input air over the cargo 26 for more effective interrogation of the interior 66 of the container 10.

Any suitable input air pump 49 may provide a positive pressure of input air to the air input exterior port 28 of the air input tubular frame member 21a. The input air pump 49 may comprise any suitable air input conduit 50 which may connect the output of the input air pump 49 to the air input exterior port 28. Input air will be delivered to the interior 66 of the shipping container from the air input tubular frame member 21a through its air input interior ports 47.

The sample air is received from the interior 66 of the container 10 through the sample air output interior ports 47 of the sample air output tubular frame member 21b. The sample air is received on the exterior of the container 10 from the sample air output exterior port 28 of the sample air output tubular frame member 21b.

Any suitable output air pump 51 may be connected to the sample air output exterior port 28 of the sample air output tubular frame member 21b. The output air pump 51 may comprise any suitable sample air output conduit 52 which may connect the input of the air pump 51 to the sample air output exterior port 28 of the sample air output tubular frame member 21b.

The sample air from the output air pump 51 may be conveyed to any suitable detection apparatus 53 by any suitable detection apparatus air conduit 54. The airflow of sample air within the container 10 is illustrated by airflow patterns 57.

The detection apparatus 53 may comprise one or more of the output air pump 51, the sample air output conduit 52, the detection apparatus conduit 54, and the sample air recycling conduit 55.

If it is desired to recycle the sample air from the detection apparatus 53 back into the container 10, then any suitable sample air recycling conduit 55 may be provided from the output of the detection apparatus 53 to the input of the input air pump 49. Recycling the sample air back into the container 10 may be advantageous if there are any hazardous substances from the cargo 26 in the sample air. On the other hand, if it is not desired to recycle the sample air back into the container 10, then the sample air recycling conduit 55 may be eliminated, and ambient fresh air in the vicinity of the input air pump 49 may be pumped into the air input tubular frame member 21a.

If the sample air is not recycled, then the sample air output of the detection apparatus 53 or the output air pump 51 may be discharged back into the ambient, preferably through one or more filters that remove any dangerous gases, vapors or particulates that may be present in the sample air.

As an alternative, the input air pump 49 and air input conduit 50 may be eliminated, in which case flow of the sample air through the container 10 may be provided only by the output air pump 51. In such a case, if recycling of the sample air is desired, then the sample air recycling conduit 55 may be connected directly to the air input exterior port 28 of the air input tubular frame member 21a.

As a further alternative, the output air pump 51 and its sample air output conduit 52 may be eliminated, in which case flow of the sample air through the container 10 may be provided only by the input air pump 49, and the detection apparatus conduit 54 for the detection apparatus 53 may be connected directly to the sample air output exterior port 28 of the sample air output tubular frame member 21b.

Figure 7:
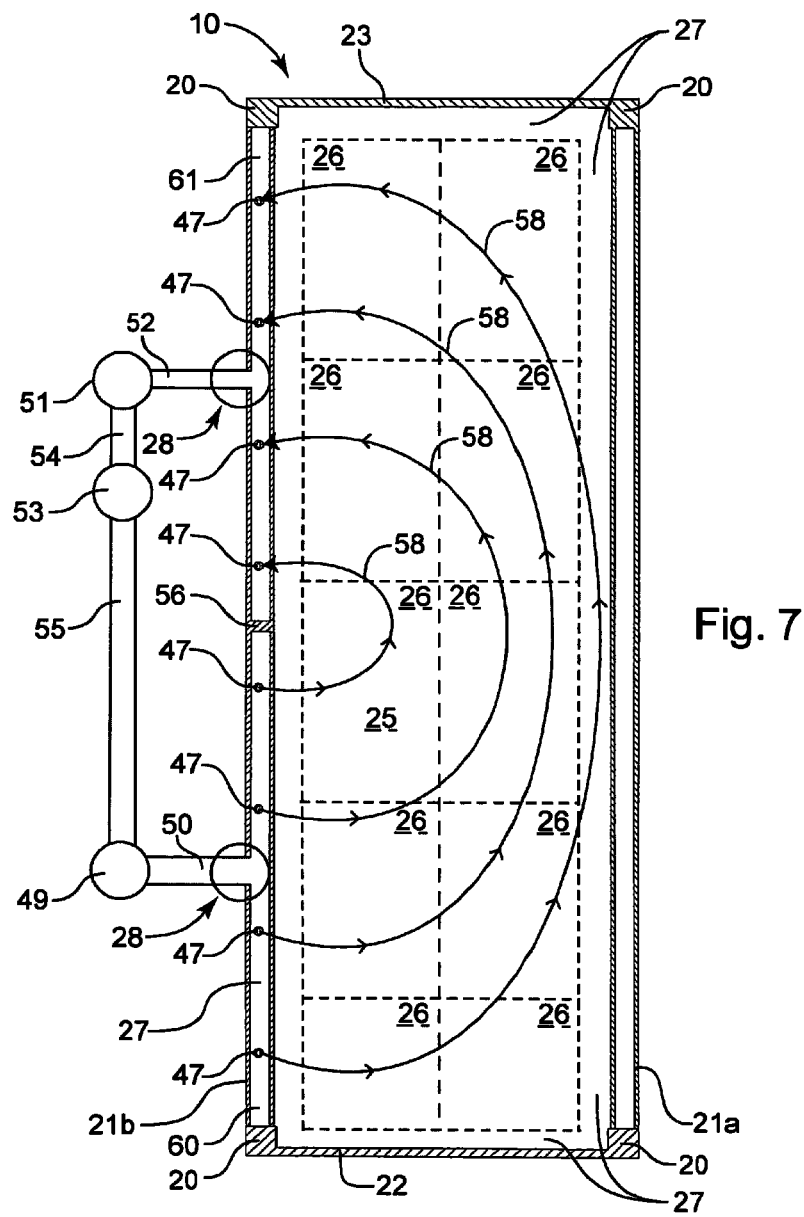
FIG. 7 is a top elevational view of the container 10 with its top removed, showing air flows 58 within the container 10, and also showing various ancillary apparatus used during interrogation of the container 10 by one tubular frame member 21b that is divided into air input and sample air output tubular frame members 60, 61 by a divider 56.

As another alternative, the locations of the output air pump 51 and the detection apparatus 53 of FIGS. 6 and 7 may be interchanged, so that it is the detection apparatus 53 that is connected to the sample air output exterior port 28 by conduit 52, and so that it is the output air pump 51 that is connected to conduits 54, 55. Such an interchange may be desirable in a case where, for example, there may be airborne particles of unauthorized materials present in the sample air, and the output air pump 51's construction is such that the airborne particles may impact and adhere to the output air pump 51's rotating parts, thereby undesirably scrubbing those airborne particles from the sampled air. Such an interchange may also be desirable in a case where, for example, any airborne particles of unauthorized materials entrained in the sample air are delicate, such as if they are entrained microorganisms, and the output air pump 51's construction is such that the delicate airborne particles might damaged if they are impacted by the output air pump 51's rotating parts.

Accordingly, when it is said that the detection apparatus 53 receives sample air from a sample air output exterior port 28, the detection apparatus may receive that sample air either directly from the sample air output exterior port 28, or indirectly from the sample air output exterior port 28 (e.g., may receive the sample air from the output of an air pump 51 whose input is connected to the sample air output exterior port 28).

Similarly, when it is said that the output pump 51 receives sample air from a sample air output exterior port 28, the output pump 51 may receive that sample air either directly from the sample air output exterior port 28, or indirectly from the sample air output exterior port 28 (e.g., may receive the sample air from the output of a detection apparatus 53 whose input is connected to the sample air output exterior port 28).

Interrogation Using One Tubular Frame Member 21A, 21B

Referring now to FIG. 7, interrogation of the container 10 using only one tubular frame member 21a, 21b will now be described. Either tubular frame member 21a, 21b by itself may be used to interrogate the container 10.

By way of example, let it be assumed that only the tubular frame member 21b will be used to interrogate the container 10. As seen, any suitable divider 56 may be installed in any suitable way in any suitable location in the air cavity 41 of the tubular frame member 21b, in order to divide the tubular frame member 21b into an air input tubular frame member 60 and a sample air output tubular frame member 61. The divider 56 may have any suitable size, shape and physical construction and may have an airtight seal with the interior surfaces of the tubular frame member 21b.

A benefit of performing interrogation of the container 10 by using only one of the tubular frame members 21a, 21b is that the overall axial pressure drops down the length of the tubular frame member 21a, 21b being used may be minimized due to the shorter axial flow lengths of its tubular frame members 60, 61, as compared to when two full length tubular frame members 21a, 21b are used to interrogate the container 10.

In addition, the flow rate of the input air or sample air through the tubular frame members 60, 61 may be desirably increased for any given input or output air pressure due to the lower flow resistance offered by the shorter tubular frame members 60, 61, thereby desirably shortening the time needed to fully interrogate the interior 66 of the container 10, as compared to when two full length tubular frame members 21a, 21b are used to interrogate the container 10.

Although the divider 56 is illustrated as dividing the tubular frame member 21b into tubular frame members 60, 61 that are of equal length, the divider may be located in the tubular frame member 21b so that the tubular frame members 60, 61 are not of equal length.

As seen in FIG. 7, the air input tubular frame member 61 has one centrally located air input exterior port 28 and four air input interior ports 47. The sample air output tubular frame member 61 has four sample air output interior ports 47 and one centrally located sample air output exterior port 28.

As an alternative, each exterior port 28 may not be centrally located in its respective tubular frame member 60, 61, and there may be more than one exterior port 28 for one or both of tubular frame members 60, 61. As a further alternative, one or both of the tubular frame members 60, 61 may have fewer or more interior ports 47 which may or may not be equally spaced from each other along the length of their respective tubular frame member 60, 61. Although only one form of exterior and interior ports 28, 47 are illustrated in FIG. 7, the exterior and interior ports 28, 47 may comprise any of the embodiments of the exterior and interior ports 28, 47 that are described herein.

Any suitable input air pump 49 may be connected by any suitable input conduit 50 to the input exterior port 28 of the input tubular frame member 60, to provide a positive input air pressure at its input exterior port 28. Any suitable output air pump 51 may be connected by any suitable output conduit 52 to the output exterior port 28 of the output tubular frame member 61, to provide a negative output air pressure at its sample air output exterior port 28. Any suitable detection apparatus 53 for the sample air from the container 10 may be connected to the output of the output air pump 51b y any suitable sampling conduit 54. The airflow within the container 10 is illustrated by airflow patterns 58.

If it is desired to recycle the sample air from the detection apparatus 53 back into the container 10, then any suitable recycle conduit 55 may be provided from the output of the detection apparatus 53 to the input of the input air pump 49. Recycling the sample air back into the container may be advantageous if there are any hazardous substances from the cargo 26 in the sample air. On the other hand, if it is not desired to recycle the sample air back into the container 10, then the recycle conduit 55 may be eliminated, and ambient fresh air in the vicinity of the input air pump 49 may be pumped into the input tubular frame member 61.

If the sample air is not recycled, then the detection apparatus 53 or the output air pump 51 may discharge the sample air back into the ambient, preferably through one or more filters that remove any dangerous gases, vapors or particulates that may be present in the sample air.

As an alternative, the input air pump 49 and input conduit 50 may be eliminated, in which case flow of the sample air through the container 10 may be provided only by the output air pump 51. In such a case, if recycling of the sample air is desired, then the recycling conduit 55 may be connected directly to the input exterior port 28 of the input tubular frame member 60.

As a further alternative, the output air pump 51 and its output conduit 52 may be eliminated, in which case flow of the sample air through the container 10 may be provided only by the input air pump 49, and the sampling conduit 54 for the detection apparatus 53 may be connected directly to the exterior port 28 of the output tubular frame member 61.

Shape of Air Discharge Openings 68 of Air Input Interior Ports 47 and Nozzles 48

The shape of the air discharge opening 68 in an air input interior port 47 without a nozzle 48, and the shape of the air discharge opening 68 in an air input nozzle 48 will now be addressed. By way of example, the shape of the air discharge opening 68 in an air input interior port 47 without a nozzle 48 will be discussed below, it being understood that the same comments may apply equally well to the shape of the air discharge opening 68 in an air input nozzle 48.

The air discharge opening 68 of an air input interior port 47 may have any suitable size and shape. For example, it has been discovered that it may be desirable to deliver a jet of input air from the air discharge opening 68 into the interior 66 of the container 10 so that the input air jet travels into the interior 66 for the longest possible distance. This may be desirable because it may minimize the number of air input interior ports 47 that may be needed in order to adequately interrogate the interior 66 of any given container 10. In addition, it may also increase the area within the interior 66 that may be adequately stirred by the input air jet delivered by any given air input interior port 47, for better interrogation of the container 10.

In general, the quality and speed of the interrogation of sample air from the interior 66 of the container 10 will increase as a function of the thoroughness with which the input air jets cover the interior 66; with the quality and speed of the interrogation increasing as the thoroughness with which the input air jets cover the interior 66 increases. This is because if the input air jets do not thoroughly cover any part of the interior 66, then the chances that the sample air from the interior 66 may have picked up any gasses or any airborne particles from all of the unauthorized material in the container 10 will decrease, and vice versa.

In addition, the quality and speed of the interrogation of sample air from the interior 66 will increase as a function of the thoroughness with which the input air jets stir the air within the interior 66. Such stirring may be beneficial because it may enable the input air jets to interact with the exposed inner surfaces of the container 13 and with the exposed outer surfaces of the cargo 26, and enable the input air jets to remove from them and entrain at least some of any particles of unauthorized material that may be present on them. Accordingly, the quality and speed of the interrogation may increase as the thoroughness with which the input air jets stir the air within the interior 66 increases, and vice versa.

One might suppose that a turbulent input air jet delivered from an air input interior port 47 that had a circular air discharge opening 68 would be optimum in this regard. However, it has been discovered that, under most conditions, a turbulent input air jet delivered by a rectangular air discharge opening 68 will travel further into the interior 66 of the container 10, and more adequately stir the air within the interior 66, than a turbulent input air jet delivered by a circular air discharge opening 68.

This is because, as is known, the centerline velocity $V_{cl}$ of a circular cross-section submerged turbulent air jet from a circular air discharge opening 68 may be given approximately by the following equation:

$$V_{cl} = \frac{0.96 Q_a}{0.071\left(\frac{X}{R}\right) + 0.29} \text{ where } \frac{X}{R} \rangle 9.4$$

In the above equation $Q_a$ is the average volumetric air flow per unit area for the air discharge opening 68 of the air input interior port 47, R is the radius of the air discharge opening 68, and X is the distance from the air discharge opening 68.

Similarly, it is known that the centerline velocity $V_{cl}$ for a rectangular cross-section submerged turbulent air jet from a rectangular air discharge opening 68 may be given approximately by the following equation:

$$V_{cl} = \frac{1.2 Q_a}{\sqrt{0.11\left(\frac{X}{B}\right) + 0.41}} \text{ where } \frac{X}{B} \rangle 9.4$$

In the above equation, B is equal to one-half of the height of the rectangular air discharge opening 68. It is assumed that the aspect ratio of the rectangular air discharge opening 68 (i.e., the ratio of its width to its height) is at least 3:1, so that the end effects of the rectangular air discharge opening 68 are relatively negligible.

Figure 8:
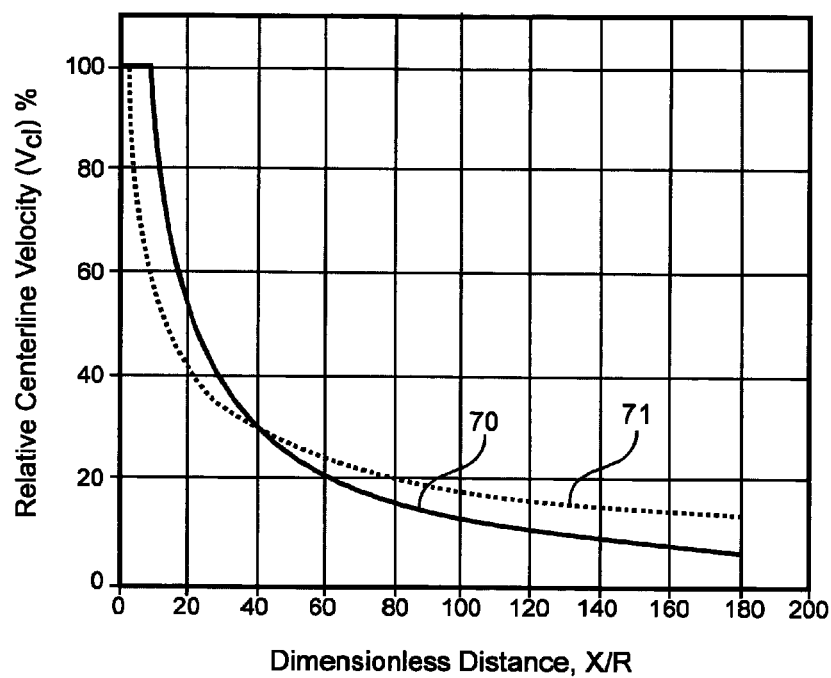
FIG. 8 is a graph illustrating the effect the shape of a submerged, turbulent air jet has on its velocity versus distance.

Referring now to FIG. 8, curves 70, 71 show, respectively, the relative centerline velocity ($V_{cl}$) of submerged circular and rectangular cross-section turbulent air jets as a function of the dimensionless distance X/R or X/B, for circular and rectangular air discharge openings 68 having the same cross-sectional area, wherein the rectangular air discharge opening 68 has an aspect ratio of 10:1.

FIG. 8 shows that although a circular cross-section air jet briefly holds its initial velocity longer than does a rectangular cross-section air jet, the velocity of the circular cross-section air jet later falls more rapidly with distance from the air discharge opening 68 than does the velocity of the rectangular cross-section air jet. Thus, a rectangular cross-section air jet may offer the benefit of traveling a greater total distance from the air discharge opening 68 than does a circular cross-section air jet. This may be because the circular cross-section air jet viscously interacts with stagnant surrounding air in a three dimensional manner, thereby slowing it down faster as compared to a rectangular cross-sectional air jet that viscously interacts with stagnant surrounding air primarily in a two dimensional manner.

It has been discovered that this benefit of a rectangular cross-section air jet may be enhanced (i.e., the air jet may travel even further into the interior 66 of a container 10 than would otherwise be the case), if an air input interior port 47 has a rectangular air discharge opening 68 that discharges a rectangular cross-section air jet into the interior 66 close to, and at least generally parallel to, the top wall 13 of the container 10. Preferably, in order to significantly obtain this enhanced benefit, the top of the rectangular air discharge opening 68 may be located a vertical distance from the top wall 13 of the container 10 that is not greater than about 10 times the height of the rectangular air discharge opening 68, and may have an aspect ratio that is at least 3:1.

It is theorized that this enhanced benefit may be obtained because viscous losses on the top side of an air jet that is located near the top wall 13 of the container 10 may be reduced because the amount of stagnant air between the top side of the air jet and the top wall 13 may be less than would be the case if the air jet were immersed in an infinite sea of air (i.e., if the air jet were located further from the top wall 13 than about 10 times the height of the rectangular air discharge opening 68).

It has been further discovered that if the rectangular air discharge opening 68 is located a vertical distance from the top wall 13 of the container 10 that is not greater than about 10 times the height of the rectangular air discharge opening 68, then the additional benefit may be obtained that the rectangular air jet may then be able to advantageously remove from the inner surface of the top wall 13, and entrain, at least some of any particles of unauthorized materials that may have attached themselves to the inner surface of the top wall 13. This may result in quicker, more sensitive interrogation of the container 10.

It is to be understood that although the above discussion was made with respect to circular and rectangular cross-section air flows that were turbulent, the same or similar comments may be made with respect to laminar circular and rectangular cross-section air flows from the air input interior ports 47.

In addition, the term "rectangular" is used broadly with respect to the shape of the air discharge opening 68 and the cross-sectional shape of the air jet, since their shapes need not be exactly rectangular. Accordingly the term "rectangular" is defined to encompass any geometric or non-geometric shape as long as the average aspect ratio of the shape, as integrated across its width, is at least about 3:1. For example a discharge opening 68 may still be "rectangular" under the above definition even though its top and bottom surfaces may be somewhat arcuate, sinuous or zigzag, rather than being straight.

Vibrating the Top Wall 13 of a Container 10

If a container 10 contains unauthorized materials in a solid or liquid form, then particles of such unauthorized materials may have attached themselves to the inner surface of the top wall 13 of the container 10 while the unauthorized materials were stored or transported in the container 10.

Accordingly, before or during interrogation of the container 10, it may be useful to vibrate the top wall 13 in order to loosen or free at least some of such attached particles of unauthorized materials from the interior surface of the top wall 13. This may then permit the jets of input air from the air input interior ports 47 or the air input nozzles 48 to entrain any loosened or freed particles of unauthorized materials; thereby making such particles of unauthorized materials part of the sample air that may then be received from the container 10 for collection, observation, identification, examination, testing or analysis by any suitable detection apparatus 53.

As an added benefit, when the top wall 13 is vibrated it may project acoustic waves downwardly into the interior 66 of the container 10, where the acoustic waves may then loosen or free at least some of any particles of unauthorized materials that may have attached themselves to the exterior surfaces of the cargo 26 or to the interior surfaces of the container 10's bottom 12, walls 14-16, or doors 17. This may then permit the jets of input air from the air input interior ports 47 or the air input nozzles 48 to entrain any such loosened or freed particles of unauthorized materials; thereby making such particles of unauthorized materials part of the sample air that may then be removed from the container 10 for collection, observation, identification, examination, testing or analysis by any suitable detection apparatus 53.

One or more of any suitable vibration apparatus 75 may be used to vibrate the top wall 13 in any suitable way; may be located in any suitable respective locations on the top wall 13, and may be permanently or removably mounted to the top wall 13 in any suitable way. A vibration apparatus 75 may comprise, for example, any suitable electrical, mechanical, pneumatic or hydraulic vibrator having any suitable size, shape, power source, and construction.

To minimize the power needed by the vibration apparatus 75 to vibrate the top wall 13 adequately, it may be advantageous to vibrate the top wall 13 at its fundamental resonant frequency, or at a harmonic thereof. However, since a typical container 10 may be much longer than it is wide, and since its two sidewalls 14, two side bottom frame members 19, and two top, side frame members 21a, 21b impart significant axial stiffness to the container 10, it may be preferable for the vibration apparatus 75 to excite laterally directed resonances, or harmonics thereof, in the top wall 13. In that case the two top, side frame members 21a, 21b may act as elongated stationary pivots and the top wall 13 may act essentially as an elastic beam or plate that spans the gap between the two top, side frame members 21a, 21b. The fundamental resonant frequency for a top wall 13 may be in the range of from about 10 Hz to about 100 Hz, which is also a useful frequency range for exciting resonances, or harmonics thereof, within the interior 66 of the container 10.

Figure 9:
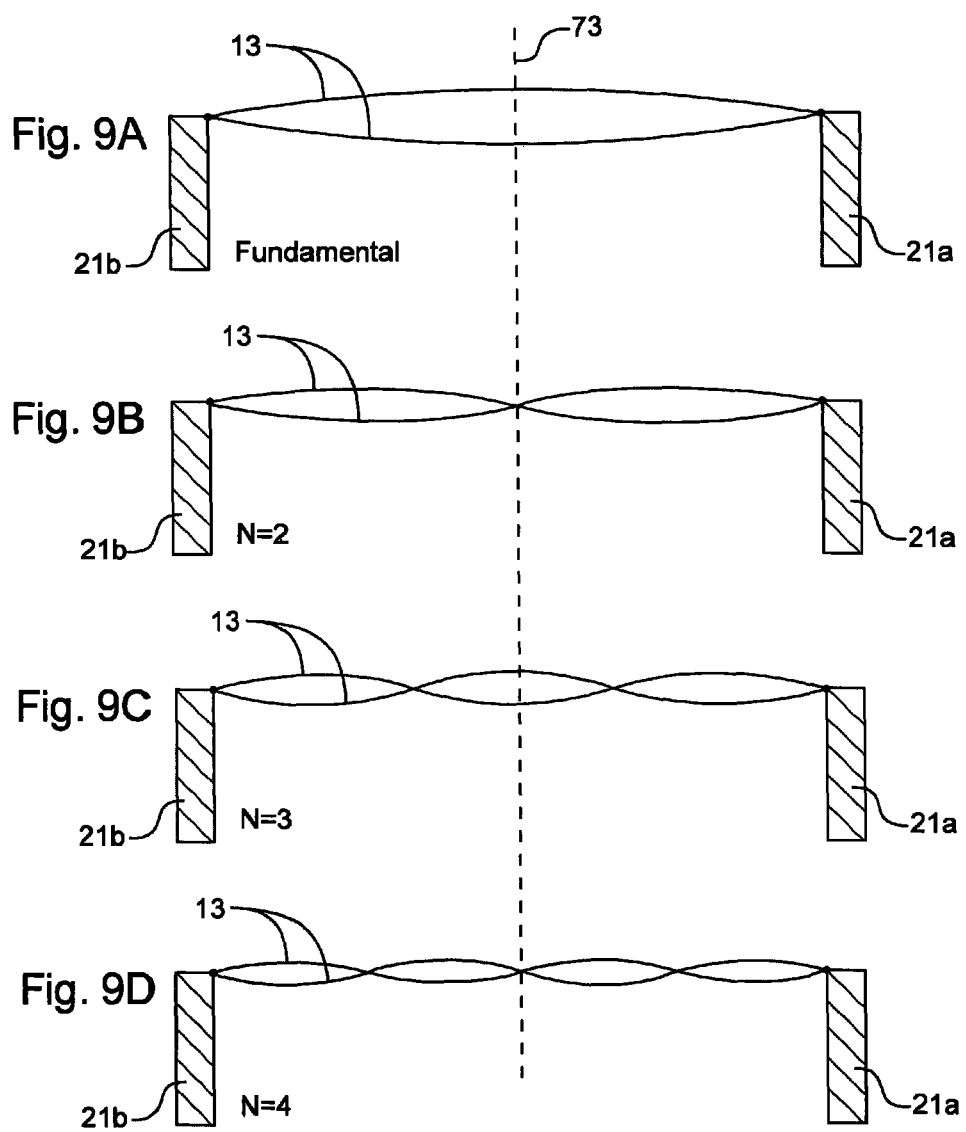
FIGS. 9A-9D are diagrammatic illustrations of the characteristic ranges of vertical motion of the top wall 13 of the container 10 for the fundamental resonance and the first three overtones, N=2, 3, 4 of the top wall 13.

It may be generally preferable that the vibration apparatus 75 be located on, or at least close to, a geometric longitudinal centerline 73 of the top wall 13 that is situated halfway between the two sidewalls 14 of the container 10. FIG. 9 shows the characteristic range of vertical motion of the top wall 13 for its fundamental resonance and for its first three harmonics, N=2, 3, 4 when a time-periodic force is applied along the centerline 73 by the vibration apparatus 75.

The vibration apparatus 75 may apply a time-periodic vertical force to the centerline 73 in order to excite the top wall 13's fundamental resonance and its odd harmonics (N=3, 5, 7, . . . ). Such a time-periodic vertical force may be applied to the top wall 13 by any suitable vibration apparatus 75. For example, such a vibration apparatus 75 may comprise an electromagnet mounted to the top wall 13; a reciprocating linear motor mounted vertically to the top wall 13; or a hydraulic or electric linear actuator mounted vertically to the top wall 13.

However, the even harmonics of the top wall 13's fundamental resonance, where N=2, 4, 6, . . . will not respond well to a time-periodic vertical force applied along the centerline 73 by a vibration apparatus 75, since the centerline 73 is, in theory, stationary for the even harmonics. Nevertheless, it has been discovered that a vibration apparatus 75 that applies a time-periodic lateral rocking motion to the top wall 13 with respect to its centerline 73, may induce the even harmonics of the top wall 13's fundamental resonance very well.

A time-periodic lateral rocking motion of the top wall 13 with respect to its centerline 73 is one where portions of the sides of the top wall 13 that are near its centerline 73 are periodically moved up and down with respect to the centerline 73 and with respect to each other, i.e., when a portion of the side of the top wall 13 that is on one side of the centerline 73 is moved up by the vibration apparatus, then the corresponding portion of the side of the top wall 13 that is on the other side of the centerline 73 is moved down by the vibration apparatus; and vice versa, while there is no significant movement of the portion of the top wall 13 along the centerline 73.

In addition, it is clear that the even harmonics experience the largest change in slope of any point along a resonance profile, as seen in FIG. 9.

Figure 10:
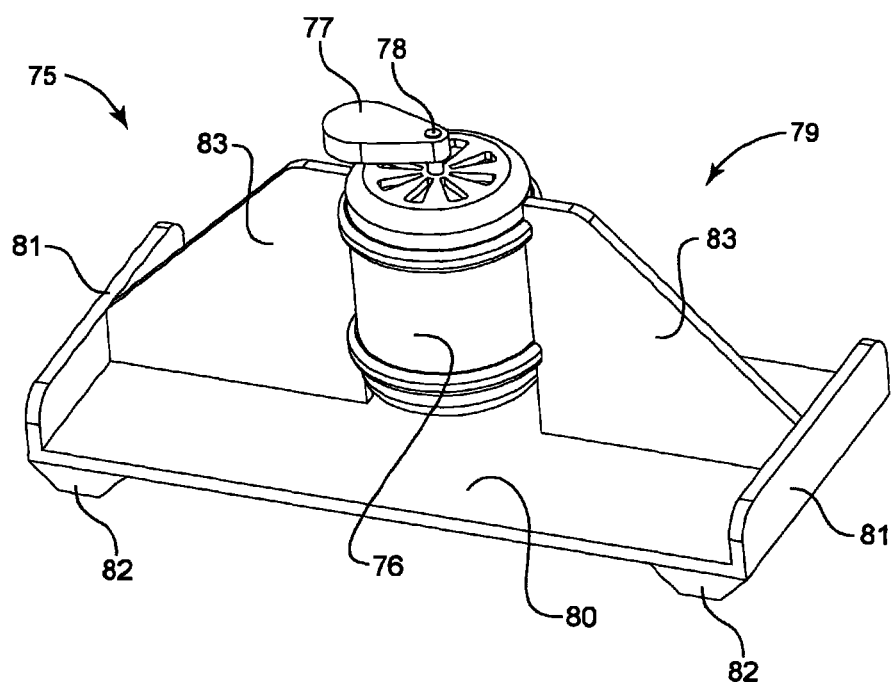
FIG. 10 is a diagrammatic perspective view of a vibration apparatus 75.

Any suitable vibration apparatus 75 may create a time-periodic lateral rocking motion of the top wall 13 with respect to its centerline 73. For example, as seen in FIG. 10, the vibration apparatus 75 may comprise a motor 76 with an eccentric rotational weight 77 mounted to its output shaft 78; and any suitable mounting frame 79 with stiffening features that can assist in faithfully transmitting any forces or torques developed by eccentric rotational weight 77, to the top wall 13 of container 10. The mounting frame 79 may have any suitable size, shape and construction, and may comprise, for example, a rectangular base plate 80, a pair of reinforcing ribs 81 for the ends of the base plate 80, optional feet 82, and a pair of motor mounts 83 for attaching the motor to the base plate 80 and ends 81. The motor and the various components of the mount 79 may be secured together in any suitable way, such as by the use of welding, adhesives or fasteners. It is understood that any other suitable vibration apparatus 75 may be used to impart a time-periodic lateral rocking motion of the top wall 13 with respect to its centerline 73.

To use the vibration apparatus 75, it may be permanently or removably mounted to the top wall 13 of the container 10 in any suitable location, in any suitable way, such as by the use of electromagnets, welding, adhesives, or fasteners. For example, when the frame 79 is mounted to the top wall 13, the output shaft 78 of the motor 76 may be oriented at least generally perpendicular with respect to the plane of the top wall 13, and the longitudinal centerline of the base plate 80 may be located at least generally above and at least generally parallel to the centerline 73 of the top wall 13.

When the motor 76's output shaft 78 rotates, a sinusoidal time-periodic lateral rocking force is created by the rotating eccentric weight 77. This rocking force is then transferred to the top wall 13 by the frame 79, to cause a time-periodic lateral rocking motion of the top wall 13. The great axial stiffness of the frame 79 and of the top wall 13 in the long direction of the container 10 minimize any time-periodic motion being induced in the top wall 13 in that direction. Since the time-periodic force generated by the rotating eccentric weight 77 is primarily parallel to the plane of the top wall 13, the vibration apparatus 75 is capable of exciting even harmonics in the top wall 13 in a direction that is at least generally at a right angle with respect to the centerline 73, but is not capable of exciting significant odd harmonics in the top wall 13, since odd harmonics require the application of a time-periodic force perpendicular to the plane of the top wall 13.

One advantage of a vibration apparatus 75 that creates a time-periodic lateral rocking motion of the top wall 13 with respect to its centerline 73 is the fact that such a vibration apparatus 75 may be entirely mounted directly to the top wall 13. In contrast, a vibration apparatus 75 that creates a time-periodic vertical motion of the centerline 73 may need to be mounted to a mechanically stiff reference structure that is separate from the container 10. Additionally, a vibration apparatus 75 that creates a time-periodic lateral rocking motion of the top wall 13 with respect to its centerline 73 may not be subjected to as large internal forces during operation and may have a longer operating life, as compared to a vibration apparatus 75 that creates a time-periodic vertical motion of the centerline 73. Finally, a rocking motion-producing vibration apparatus 75 is uniquely suited to excite even modes of vibration in the top wall 13 of a container 10.

All of the disclosures herein regarding the vibration apparatus 75 and its use with a container 10 may be applied to any container 10, regardless of whether or not one or more of the frame members 18 of the container 10 are being used as air ducts to deliver input air into the interior 66 of the container 10, or to receive sample air from the interior 66.

Ports 85-92 in the Walls 13-15 of the Container 10

Figure 11:
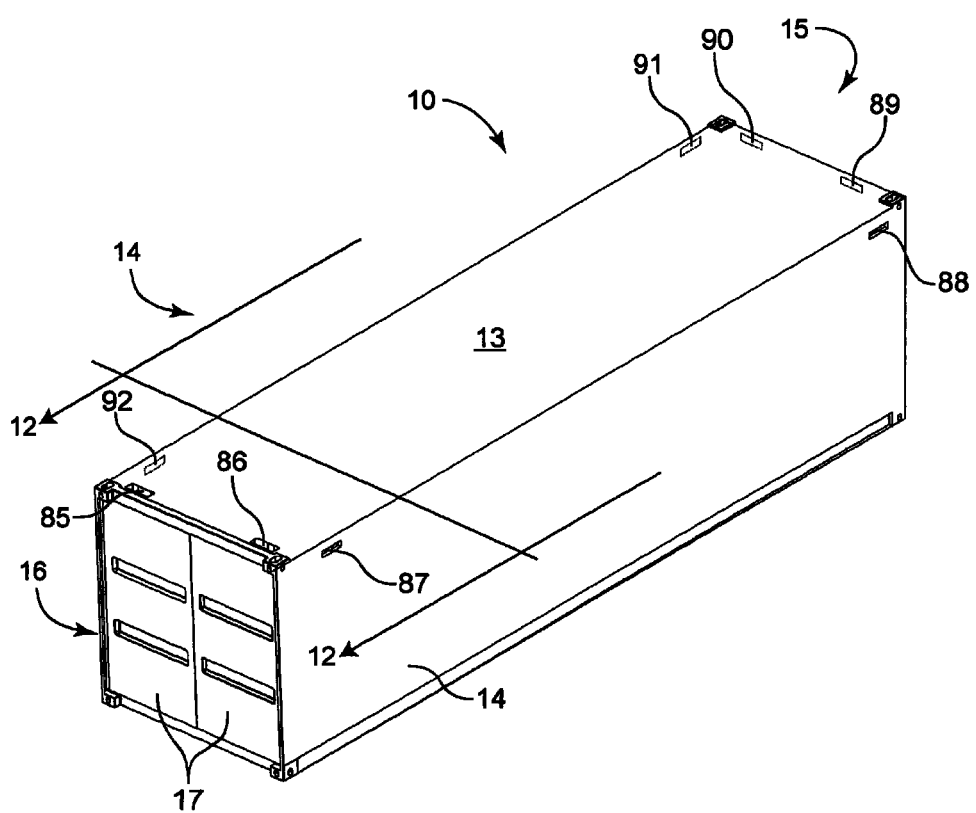
FIG. 11 is a perspective view of a container 10 having ports 85-92 in its walls 13-15.
Figure 12:
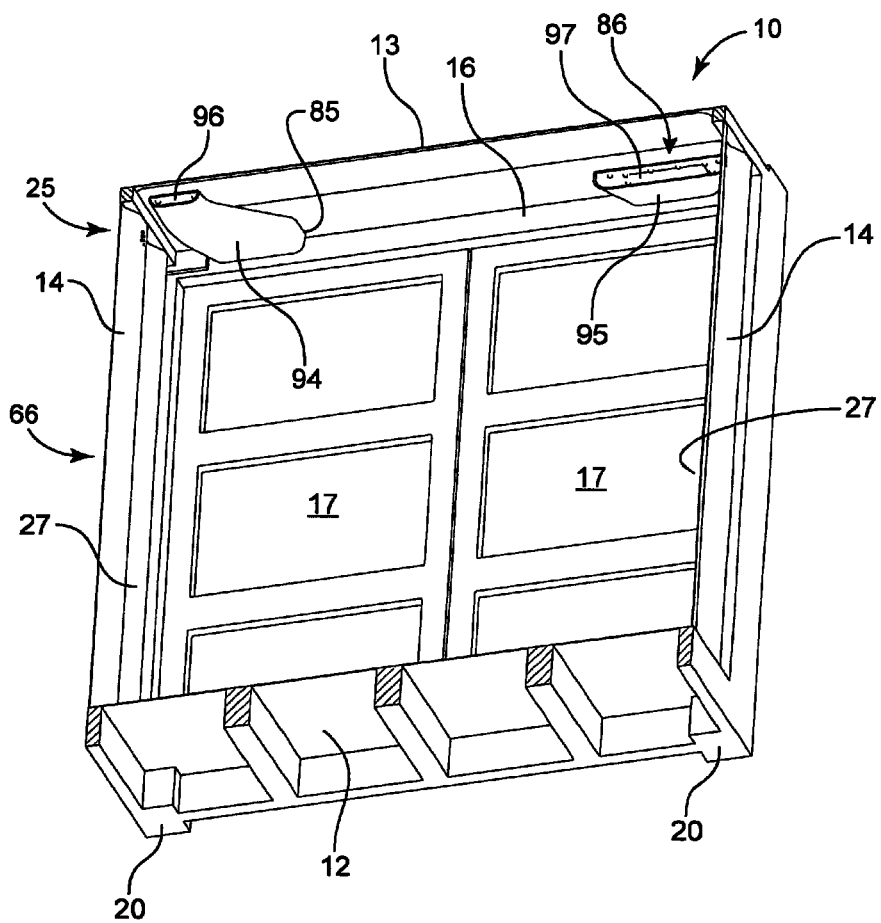
FIG. 12 is a perspective view of a container 10 taken along line 12-12 of FIG. 12.

Turning now to FIGS. 11-12, it is seen that a container 10 may have one or more air transfer ports 85-92 in its walls 13-15. One or more of the ports 85-92 may have an input air nozzle 94 or a sample air output nozzle 95. The nozzles 94, 95 may be used interchangeably, in that the nozzle 94 may be used as a sample air output nozzle 94, and the nozzle 95 may be used as an input air nozzle 95.

The walls 13-15 of the container 10 may have none of the ports 85-92, one of the ports 85-92, or two or more of the ports 85-92. The ports 85-92 may be placed in any suitable location in the walls 13-15 so as to be operable to access the top air space 25 or a lateral air space 27 within the interior 66 of the container 10.

The container 10's doors 17 may be provided with one or more ports and nozzles that are the same as the ports 85-92 or nozzles 94-95.

Although the ports 85-92 penetrate the walls 13-15 of the container 10, they do not necessarily penetrate the container 10's frame 18.

Any particular port 85-92 may have any suitable size, construction and location; may be operable to be used as an air input exterior port 85-92 to deliver air or recycled sample air to the interior 66 of the container 10; or may be operable to be used as a sample air output exterior port 85-92 to receive sample air from the interior 66 of the container 10. Any particular port 85-92 may, or may not, have the same size and construction as any of the other ports 85-92.

Any particular port 85-92 may have any suitable geometric or non-geometric shape, such as round or rectangular. Any particular port 85-92 may, or may not, have the same shape as any of the other ports 85-92. If an air input exterior port 87-92 in the walls 14-15 has a rectangular shape, then it may have an aspect ratio of at least about 3:1 and may be located a vertical distance from the top wall 13 of the container 10 that is not greater than about 10 times the height of the rectangular port 85-92. If an air input exterior port 85-86 in the top wall 13 is rectangular, then it may also have an aspect ratio of at least about 3:1.

When an air input exterior port 85-92 is described as having a rectangular shape, it is meant that at least its air discharge opening into the interior 66 of the container 10 has a rectangular shape, since it is conceivable that it might have a different shape upstream from its air discharge opening.

The term "rectangular" is used broadly with respect to the shape of the ports 85-92, the shape of the air discharge opening 96 of the nozzle 94, and the shape of the air jets they produce when being used as an air input port or nozzle, since their shapes need not be exactly rectangular. Accordingly the term "rectangular" is defined with respect to the ports 85-92 and air discharge opening 96 to encompass any geometric or non-geometric shape as long as the average aspect ratio of the shape, as integrated across its width, is at least about 3:1. For example an air input exterior port 85-92 or air discharge opening 96 may still be "rectangular" under the above definition even though its top and bottom surfaces may be somewhat arcuate, sinuous or zigzag, rather than being straight.

It is to be understood that the above disclosures regarding laminar and turbulent circular and rectangular cross-section air flows from the air input interior ports 47 and nozzles 48 may apply equally well to any air input port exterior ports 85-92 and any air input nozzle 96.

As best seen in FIG. 12, if the port 86 in the top wall 13 of the container 10 is an air input exterior port 86, then it may comprise an air input nozzle 94 having an air discharge opening 96 for delivering input air into the interior 66 of the container 10. Similarly, if the port 85 in the top wall 13 of the container 10 is a sample air output exterior port 85, then it may comprise a sample air output nozzle 95 having a sample air output opening 97 for receiving sample air from the interior 66.

The nozzles 94, 95, may have any suitable size, shape and construction. Any particular nozzle 94-95 may, or may not, have the same size, shape and construction as any of the other nozzles 94-95; any particular air discharge opening 96 may, or may not, have the same size and shape as any of the other air discharge openings 96; and any particular sample air receiving opening 97 may, or may not, have the same size and shape as any of the sample air receiving openings 97.

As best seen in FIG. 12, a sample air input nozzle 94 may have a right angle bend, so that its air discharge opening 96 is at least generally at a right angle with respect to the plane of the top wall 13. This enables the air discharge opening 86 to deliver input air into the top air space 25 in the container 10 in a direction that is at least generally parallel to the top wall 13, for better interrogation of the container 10.

As is also seen in FIG. 12, a sample air output nozzle 95 may also have a right angle bend, so that its sample air output opening 97 is at least generally at a right angle with respect to the plane of the top wall 13. This enables the sample air output opening 97 to receive sample air from the top air space 25 in the container 10 in a direction that is at least generally parallel to the top wall 13, for better interrogation of the container 10.

Alternatively, the air input nozzle 94 may be shaped, located, sized and oriented so as to be operable to deliver input air into one or more of the top or lateral air spaces 25, 27 in any desired direction or pattern, and the sample air output exterior nozzle 95 may be shaped, located, sized and oriented so as to be operable to receive sample air from one or more of the top or lateral air spaces 25, 27 from any desired direction and in any desired pattern.

Any particular air input exterior port 85-92 and any particular sample air output exterior port 85-92 may be connected to one or more air pumps 49-51, conduits 50, 52, 54, and 55, and interrogation apparatus 53 so that an air input exterior port 85-92 may function in a manner that is similar to that of an air input exterior port 28 of FIGS. 6-7, and so that a sample air output exterior port 85-92 will function in a manner similar to that of a sample air output exterior port 28 of FIGS. 6-7.

For better interrogation of a container 10, an air input exterior port 85-92 and a sample air output exterior port 85-92 may be located on opposite ends of one of the walls 13-15, such as on opposite ends of the top wall 13 of the container 10, as seen in FIGS. 11-12. Alternatively, an air input exterior port 85-92 and a sample air output exterior port 85-92 may be located on opposite ends of a common wall 13-15; or may be located on respective different walls 13-15.

As further alternatives, an air input exterior port 85-92 may be used with a sample air output tubular member 21*b*, and a sample air output exterior port 85-92 may be used with an air input tubular frame member 21*a*.

It is to be understood that the specific embodiments of the claimed invention that are disclosed herein were disclosed strictly by way of non-limiting example. Accordingly, various modifications may be made to those embodiments without deviating from the scope and spirit of the claimed invention. Additionally, certain aspects of the claimed invention that were described in the context of a particular embodiment may be combined or eliminated in other embodiments. Although advantages associated with a certain embodiment of the claimed invention have been described in the context of that embodiment, other of the embodiments may also exhibit such advantages. Further, not all embodiments need necessarily exhibit any or all of such advantages in order to fall within the scope of the claimed invention.

When the phrase "at least one of" is used in any of the claims, that phrase is defined to mean that any one, any more than one, or all, of the listed things or steps following that phrase is, or are, part of the claimed invention. For example, if a hypothetical claim recited "at least one of A, B, and C", then the claim is to be interpreted so that it may comprise (in addition to anything else recited in the claim), an A alone, a B alone, a C alone, both A and B, both A and C, both B and C, and/or all of A, B and C.

Before an element in a claim is construed as claiming a means for performing a specified function under 35 USC section 112, last paragraph, the words "means for" must be used in conjunction with that element.

As used herein, except in the claims, the words "and" and "or" are each defined to also carry the meaning of "and/or".

In view of all of the disclosures herein, these and further modifications, adaptations and variations of the claimed invention will now be apparent to those of ordinary skill in the art to which it pertains, within the scope of the following claims.

What is claimed is:

1. A shipping container interrogation apparatus; wherein said interrogation apparatus comprises a shipping container; and wherein said shipping container comprises: a frame operable to provide structural rigidity and shape for said shipping container, wherein said frame comprises an air transfer tubular frame member; and
an interior; wherein said air transfer tubular frame member is operable to either receive input air and deliver said input air to said interior of said shipping container, or is operable to receive sample air from said interior of said shipping container and deliver said sample air to a location outside of said shipping container.

2. The interrogation apparatus of claim 1, wherein said air transfer tubular frame member comprises an air input tubular frame member; wherein said air input tubular frame member comprises an air input exterior port that is operable to receive said input air; and wherein said air input tubular frame member further comprises an air input interior port that is operable to deliver said input air from said air input tubular frame member to said interior of said shipping container.

3. The interrogation apparatus of claim 2, wherein interrogation apparatus further comprises an air input pump that is operable to deliver said input air to said air input exterior port of said air input tubular frame member.

4. The interrogation apparatus of claim 2, wherein said shipping container further comprises a shipping container top wall; wherein said air input interior port comprises an air discharge opening having a top and a height; and wherein said top of said air discharge opening is located within said interior of said shipping container at a vertical distance from said shipping container top wall that is not greater than about 10 times said height of said air discharge opening.

5. The interrogation apparatus of claim 2, wherein said air input interior port comprises a nozzle that is operable to direct at least part of said input air that is delivered to said interior of said shipping container in at least one of a predetermined flow direction, a predetermined flow pattern, and a predetermined turbulent flow characteristic within said interior of said shipping container.

6. The interrogation apparatus of claim 2, wherein said shipping container further comprises a shipping container top wall; wherein said air input interior port comprises a nozzle; wherein said nozzle comprises an air discharge opening having a top and a height; and wherein said top of said air discharge opening is located within said interior of said shipping container at a vertical distance from said shipping container top wall that is not greater than about 10 times said height of said air discharge opening.

7. The interrogation apparatus of claim 1, wherein said air transfer tubular frame member comprises a sample air output tubular frame member; wherein said sample air output tubular frame member comprises a sample air output interior port that is operable to receive said sample air from said interior of said shipping container; and wherein said sample air output tubular frame member further comprises a sample air output exterior port that is operable to deliver said sample air from said sample air output tubular frame member to said location outside of said shipping container.

8. The interrogation apparatus of claim 7, wherein said interrogation apparatus further comprises a sample air output pump that is operable to receive said sample air from said sample air output exterior port.

9. The interrogation apparatus of claim 7, wherein said interrogation apparatus comprises a detection apparatus that is operable to receive said sample air from said sample air output exterior port.

10. The interrogation apparatus of claim 1, wherein said shipping container comprises first and second said air transfer tubular frame members; wherein said first air transfer tubular frame member comprises an air input tubular frame member; wherein said air input tubular frame member comprises an air input exterior port that is operable to receive said input air; wherein said air input tubular frame member further comprises an air input interior port that is operable to deliver said input air from said air input tubular frame member to said interior of said shipping container; wherein said second air transfer tubular frame member comprises a sample air output tubular frame member, wherein said sample air output tubular frame member comprises a sample air output interior port that is operable to receive said sample air from said interior of said shipping container; and wherein said sample air output tubular frame member further comprises a sample air output exterior port that is operable to receive said sample air from said sample air output tubular frame member and deliver sample air to said location outside of said shipping container.

11. The interrogation apparatus of claim 10, wherein said shipping container further comprises two walls; and wherein said first and second said air transfer tubular frame members both comprise part of a common one of said two walls.

12. The interrogation apparatus of claim 10, wherein said shipping container further comprises two walls; and wherein said first and second air transfer tubular frame members each comprise part of a different one of said two walls.

13. The interrogation apparatus of claim 1 wherein said air transfer tubular frame member comprises an air cavity and an air transfer exterior port; wherein said shipping container further comprises a sidewall, wherein said sidewall comprises corrugated material that comprises a repeating array of corrugation exterior portions and corrugation interior portions; wherein adjacent pairs of said corrugation exterior portions and said corrugation interior portions are joined by respective corrugation sides; wherein said air transfer exterior port is located between an adjacent pair of said corrugation exterior portions and comprises an exterior air plenum that is in fluid communication with said air cavity of said air transfer tubular frame member.

14. The interrogation apparatus of claim 1 wherein said air transfer tubular frame member comprises an air cavity and an air transfer exterior port; wherein said shipping container further comprises a sidewall, wherein said sidewall comprises corrugated material that comprises a repeating array of corrugation exterior portions and corrugation interior portions; wherein adjacent pairs of said corrugation exterior portions and said corrugation interior portions are joined by respective corrugation sides; wherein said air transfer exterior port is located between an adjacent pair of said corrugation exterior portions and comprises a tubular element that is in fluid communication with said air cavity of said air transfer tubular frame member.

15. The interrogation apparatus of claim 1, wherein said shipping container further comprises a pair of sidewalls and a top wall; wherein said top wall has a longitudinal centerline that is situated halfway between said pair of sidewalls; and wherein said interrogation apparatus further comprises a vibration apparatus that is operable to apply a time-periodic lateral rocking motion to said top wall with respect to said longitudinal centerline while said shipping container is not being transported.

16. The interrogation apparatus of claim 1, wherein said shipping container comprises a wall; and wherein said interrogation apparatus further comprises an air transfer port in said wall that is operable to either receive said input air and deliver said input air to said interior of said shipping container or is operable to receive said sample air from said interior of said shipping container and deliver said sample air to said location outside of said shipping container.

17. A method for interrogating a shipping container; wherein said shipping container comprises a frame operable to provide structural rigidity and shape for said shipping container, wherein said frame comprises an air transfer tubular frame member; and an interior; and wherein said method comprises the step of interrogating said shipping container by using said air transfer tubular frame member for at least one of receiving input air and delivering said input air to said interior of said shipping container, and receiving sample air from said interior of said shipping container and delivering said sample air to a location outside of said shipping container.

18. The method of claim 17, wherein said air transfer tubular frame member comprises an air input tubular frame member; and wherein said method further comprises the step of using said air input tubular frame member for receiving said input air and delivering said input air to said interior of said shipping container.

19. The method of claim 17, wherein said air transfer tubular frame member comprises a sample air output tubular frame member; and wherein said method further comprises the step of using said sample air output tubular frame member for receiving said sample air from said interior of said shipping container and delivering said sample air to said location outside of said shipping container.

20. The method of claim 19, wherein said method further comprises the step of using a detection apparatus for receiving said sample air from said sample air output tubular frame member and for detecting an unauthorized material in said sample air.

21. The method of claim 17, wherein said shipping container comprises first and second said air transfer tubular frame members, wherein said first said air transfer tubular frame member comprises an air input tubular frame member; wherein said second said air transfer tubular frame member comprises a sample air output tubular frame member; and wherein said method further comprises the steps of using said air input tubular frame member for receiving said input air and delivering said input air to said interior of said shipping container; and using said sample air output tubular frame member for receiving said sample air from said interior of said shipping container and delivering said sample air to said location outside of said shipping container.

22. The method of claim 21, wherein said method further comprises the step of conveying said sample air from said sample air output tubular frame member to said air input tubular frame member.

23. The method of claim 17, wherein said method further comprises the step of delivering at least part of said input air to said interior of said shipping container in at least one of a predetermined flow direction, a predetermined flow pattern, and a predetermined turbulent flow characteristic within said interior of said shipping container.

24. The method of claim 17, wherein said shipping container further comprises a pair of sidewalls and a top wall;

wherein said top wall has a longitudinal centerline that is situated halfway between said pair of sidewalls; and wherein said method further comprises the step of applying a time-periodic lateral rocking motion to said top wall with respect to said longitudinal centerline.

25. A shipping container interrogation apparatus; wherein said interrogation apparatus comprises a shipping container; and wherein said shipping container comprises:
an interior; and an air transfer tubular frame member;
wherein said air transfer tubular frame member is operable to either receive input air and deliver said input air to said interior of said shipping container, or is operable to receive sample air from said interior of said shipping container and deliver said sample air to a location outside of said shipping container;
wherein said air transfer tubular frame member comprises an air input tubular frame member;
wherein said air input tubular frame member comprises an air input exterior port that is operable to receive said input air; and
wherein said air input tubular frame member further comprises an air input interior port that is operable to deliver said input air from said air input tubular frame member to said interior of said shipping container;
wherein said air input interior port comprises an air discharge opening having a width and a height; wherein said air discharge opening comprises a shape that is least generally rectangular; and wherein said shape has an aspect ratio of at least about 3:1.

26. A shipping container interrogation apparatus; wherein said interrogation apparatus comprises a shipping container; and wherein said shipping container comprises:
an interior; and an air transfer tubular frame member;
wherein said air transfer tubular frame member is operable to either receive input air and deliver said input air to said interior of said shipping container, or is operable to receive sample air from said interior of said shipping container and deliver said sample air to a location outside of said shipping container;
wherein said air transfer tubular frame member comprises an air input tubular frame member;
wherein said air input tubular frame member comprises an air input exterior port that is operable to receive said input air; and
wherein said air input tubular frame member further comprises an air input interior port that is operable to deliver said input air from said air input tubular frame member to said interior of said shipping container;
wherein said air input interior port comprises a nozzle; wherein said nozzle comprises an air discharge opening having a width and a height; wherein said air discharge opening comprises a shape that is least generally rectangular; and wherein said shape has an aspect ratio of at least about 3:1.

27. A shipping container interrogation apparatus; wherein said interrogation apparatus comprises a shipping container; and wherein said shipping container comprises:
an interior; and an air transfer tubular frame member;
wherein said air transfer tubular frame member is operable to either receive input air and deliver said input air to said interior of said shipping container, or is operable to receive sample air from said interior of said shipping container and deliver said sample air to a location outside of said shipping container;
wherein said shipping container comprises first and second said air transfer tubular frame members;
wherein said first air transfer tubular frame member comprises an air input tubular frame member; wherein said air input tubular frame member comprises an air input exterior port that is operable to receive said input air; wherein said air input tubular frame member further comprises an air input interior port that is operable to deliver said input air from said air input tubular frame member to said interior of said shipping container;
wherein said second air transfer tubular frame member comprises a sample air output tubular frame member, wherein said sample air output tubular frame member comprises a sample air output interior port that is operable to receive said sample air from said interior of said shipping container; wherein said sample air output tubular frame member further comprises a sample air output exterior port that is operable to receive said sample air from said sample air output tubular frame member and deliver said sample air to said location outside of said shipping container; and
wherein said interrogation apparatus further comprises a detection apparatus that is operable to receive said sample air from said sample air output exterior port, and a sample air recycling conduit that is operable to convey said sample air from said detection apparatus to said air input tubular frame member.

28. A shipping container interrogation apparatus; wherein said interrogation apparatus comprises a shipping container; and wherein said shipping container comprises:
an interior; and an air transfer tubular frame member;
wherein said air transfer tubular frame member is operable to either receive input air and deliver said input air to said interior of said shipping container, or is operable to receive sample air from said interior of said shipping container and deliver said sample air to a location outside of said shipping container;
wherein said shipping container further comprises a pair of sidewalls and a top wall; wherein said top wall has a longitudinal centerline that is situated halfway between said pair of sidewalls; wherein said interrogation apparatus further comprises a vibration apparatus that is operable to apply a time-periodic lateral rocking motion to said top wall with respect to said longitudinal centerline; and
wherein said time-periodic lateral rocking motion is used to excite even harmonics of said top wall of said shipping container in a direction that is at least generally at about a right angle with respect to said longitudinal centerline.

29. A method for interrogating a shipping container; wherein said shipping container comprises an interior, an air transfer tubular frame member, a pair of sidewalls, and a top wall; and wherein said method comprises the steps of:
(a) using said air transfer tubular frame member for at least one of receiving input air and delivering said input air to said interior of said shipping container, and receiving sample air from said interior of said shipping container and delivering said sample air to a location outside of said shipping container;
(b) applying a time-periodic lateral rocking motion to said top wall with respect to said longitudinal centerline; and
(c) using said time-periodic lateral rocking motion for exciting even harmonics of said top wall of said shipping container in a direction that is at least generally at about a right angle with respect to said longitudinal centerline.

* * * * *